(12) United States Patent
Yampolsky et al.

(10) Patent No.: US 11,426,300 B2
(45) Date of Patent: Aug. 30, 2022

(54) MOTORIZED TIGHTENING MECHANISM FOR THE SCOLIOSIS BOSTON BRACE

(71) Applicants: Sabina Vaysburd Yampolsky, Los Angeles, CA (US); Amaan Irfan Furniturewala, Los Angeles, CA (US)

(72) Inventors: Sabina Vaysburd Yampolsky, Los Angeles, CA (US); Amaan Irfan Furniturewala, Los Angeles, CA (US)

( * ) Notice: Subject to any disclaimer, the term of this patent is extended or adjusted under 35 U.S.C. 154(b) by 56 days.

(21) Appl. No.: 16/578,404

(22) Filed: Sep. 23, 2019

(65) Prior Publication Data

US 2020/0179152 A1  Jun. 11, 2020

(51) Int. Cl.
*A61F 5/02* (2006.01)

(52) U.S. Cl.
CPC .............. *A61F 5/024* (2013.01); *A61F 5/022* (2013.01)

(58) Field of Classification Search
CPC .. A61F 5/028; A61F 5/02; A61F 5/026; A61F 5/03; A61F 2250/001; A61F 5/01; A61F 5/022; A61F 5/058; A61F 5/0102; A61F 5/0193; A61F 2005/0155; A61F 2005/0188; A61F 5/0104; A61F 13/00038; A61F 2005/0183; A61F 2005/0197; A61F 2007/0024; A61F 2007/0228; A61F 2220/0025; A61F 2220/005; A61F 2250/0004; A61F 2250/006; A61F 5/08; A61F 5/3715; A61F 5/024; A61H 1/00; A61H 2205/081; A61H 2201/1623
See application file for complete search history.

*Primary Examiner* — Ophelia A Hawthorne

(57) ABSTRACT

An improved Scoliosis Boston Brace having a motorized tightening mechanism is disclosed, which tightens the brace around the patient's body with a motorized mechanism. The motorized tightening mechanism makes it easier for the patient to tighten the brace around their body, and also eases the task of putting on/off, the brace. The components of the present invention include a Boston brace, a worm drive, worm drive rack, a hexagonal peg, nylon strap, rivet, two parts epoxy glue, buttons and motor screwdriver. The worm drive and the worm drive rack are connected to the nylon strap, which is attached through rivet to the Boston brace. The hexagonal peg helps in manipulating the worm drive, which determines the tightens of the brace and the button attached to worm drive rack, helps to unclasp the mechanism when taking off the brace.

8 Claims, 4 Drawing Sheets

MOTORIZED TIGHTENING MECHANISM FOR THE SCOLIOSIS BOSTON BRACE

FIELD OF THE INVENTION

The present invention generally relates to the external body braces and, more particularly to a motorized tightening mechanism which can bp used along with the Scoliosis Boston Brace, which enables automatically tightening of the Scoliosis brace around the user's body without any manual intervention.

BACKGROUND OF THE INVENTION

Scoliosis is a medical condition which is associated with an abnormally curved spine. In this condition, a person's spine has a sideways curve, which is usually "S" or "C" shaped. A healthy person's spine constitutes a straight line together with the head and legs when viewed from the front or back. Scoliosis is of two types, i.e. functional scoliosis, which results from bad postures or trauma but involves no structural change of the spine, and structural scoliosis, which involves a structural change of the spine. The exact cause of the scoliosis is not known till date, but if the condition worsens, then it might lead to failure of heart or lungs. The curve of the spine can be stable or can increase over time. Initial stages of scoliosis or mild scoliosis does not typically cause any problems, while severe cases can interfere with breathing. Scoliosis is a progressive disease which can have severe adverse effects on the patient's life, both physically and mentally.

There are many efficient ways of treating scoliosis. The treatment of scoliosis mainly depends on the degree of curve of the spine, location, and cause and many more. Minor curves of the spice can be treated using bracing or surgery. Bracing is a method where the brace must be fitted to the person and used daily until growing stops. Another possible method of treating or managing scoliosis is surgery. Unfortunately, scoliosis surgery can be very risky. Less invasive methods of treating or managing scoliosis has traditionally included physical therapy, chiropractic therapy, or bracing, among other things.

Some previous braces have been made to provide improved comfort, support, or customizability to individual wearers. The conventional braces which are used for treating scoliosis includes a support unit for protecting the patient's waist which comprises of straps to hold on to the patient's body and a retaining unit for retaining the support unit on the waist which comprises of sealing mechanism such as a Velcro. When a scoliosis brace is worn around the body of the patient, the straps which are present on the support unit supports the lumbar vertebrae, and the Velcro firmly retains the brace to apply pressure to the lumbar vertebra at a certain angle.

But there are several problems which are associated with the conventional braces. As the spinal curve seen in different patients are different, the brace remains same for each patient and the force or pressure applied to the spine also remains same. The degree of the curve of the spinal column requires the brace to be fixed at a set correction angle, which is not possible with the conventional brace. Also if the brace has to be customized to each and every patient, according to the degree of the disease, then it requires high amount of money, time, and effort, and is not feasible to everyone.

US Patent no 20130303955 A1 discloses an Off-the-shelf adjustable brace for treating scoliosis and associated methods. The adjustable scoliosis brace is for treating a spinal curve in a patient and includes front and back vertical support pillars each having a longitudinal connection plate including upper and lower variable connection portions, and a rotatable arm coupled to the upper variable connection portions. A girdle device is coupled to the front and back vertical support pillars. The girdle device includes waist engaging members contoured to inhibit movement of the brace on a waist of the patient, adjustable coupling features configured to couple the plurality of waist engaging members together, and variable connection features configured to couple the plurality of waist engaging members to the longitudinal connection plates. An upper thoracic pad is configured to be coupled between the rotatable arms. A lower thoracic pad is configured to be coupled between the longitudinal connection plates of the front and back vertical support pillars.

U.S. Pat. No. 7,766,850 B2 discloses a de-rotational brace for treatment of idiopathic scoliosis. A brace for correction of scoliosis is disclosed, comprising at least one thoracic shell element and a pelvic shell element and at least one working element having a main longitudinal axis to be oriented parallel to the trunk to be treated, anchored on one of its opposite ends to the thoracic shell element and on the other to the pelvic shell element, and having spring characteristics adapted to apply continuous de-rotational force about said longitudinal axis.

U.S. Pat. No. 8,066,653 B2 discloses a scoliosis brace having angle adjustment unit having an angle adjustment unit and a plurality of support units connected to one another so that the relative position can be changed to support different parts of a human body. The body is pressurized according to the relative position of respective support units so that the spinal column is corrected precisely.

US Patent no 20150018736 A1 discloses a Scoliosis Brace which comprises a belt and removably attachable vertical strut(s). Each vertical strut can comprise one or more of a strut(s), thoracic pad(s), hip pad(s), lumbar support pad(s), chest support pad(s), de-rotation pad(s), or any other component suitable to assist or restrict movement of a wearer's body, reduce or apply a force to a wearer's body, correct the shape of a wearer's body, reduce pain, or provide support to a wearer's body. It is contemplated that each component can be removable or adjustable from a vertical strut or belt.

U.S. Pat. No. 6,676,617 B1 discloses a body brace with a motorized tightening mechanism. The adjustable, removable, interlocking iliac crest belt for a body brace is disclosed. The belt can be secured to the inside of a posterior portion of the body brace, and is secured about the patient's waist and upper hip region, engaging the iliac crests of the patient and providing additional pressure and stabilization force. Adjustable hook and loop fastening elements can be used to fasten the iliac crest belt. The belt is intended for use in body braces of the type for immobilizing or stabilizing a patient's spine in a post-surgical therapeutic application, or for treating abnormal spinal curvature, which brace may include body-conforming front and back shell elements molded from plastic, and adjustable strap elements affixed thereto for attaching the shells together around the torso of the patient with a selected compressive force.

Unfortunately, none of the above prior art patents provides a brace which can provide support and comfort to all kinds of patients. Also none of the prior are patents and the currently available products provides a motorized tightening mechanism, so that the patients can wear the braces without the help of any other person. Therefore there is a need for improved scoliosis braces, which can provide a motorized self-tightening mechanism, along with high comfort and support.

OBJECTIVES OF THE INVENTION

The primary object of the present invention is to provide an improved scoliosis brace having a motorized tightening mechanism with the help of a motor.

Another object of the present invention is to provide an improved scoliosis brace which aids in the treatment of curvatures of the spine.

Another object of the present invention is to provide an improved scoliosis brace which can be worn by the patients without any external help, and also tighten it automatically.

Another object of the present invention is to provide an improved scoliosis brace that is simple to manufacture, having few components which can be assembled easily.

Another object of the present invention is to provide an improved scoliosis brace with a motorized tightening mechanism which can tighten itself correctly, thus reducing the chances to the patient requiring surgery.

SUMMARY OF THE INVENTION

The present invention provides an improved Scoliosis Boston Brace having a motorized tightening mechanism, which tightens the brace around the patient's body with a motor. The present invention provides solution to the lack of compliance with the current tightening technique present in the Boston scoliosis brace, which causes many adolescents with scoliosis to either not tighten the brace to the maximum degree or not wear it enough.

The present invention comprised of a motorized tightening mechanism, which not only makes it easier for the patient to tighten the brace around their body, but also eases the task of putting on/off the brace. The motorized tightening mechanism of the scoliosis brace ensures that the brace is tightened firmly, which leads to a higher chance of brace success and helps to avoid spine surgery. Braces are the better solution to scoliosis rather than opting for a surgery. The present invention provides an improved tightening technique which is a self-tightening technique that makes the product automatic, easy to put on and easy to tighten. It is also more accurate because it relies on technology rather than manual tightening.

The components of the present invention includes a Boston brace, a worm drive, worm drive rack, a hexagonal peg, nylon strap, rivet, two parts epoxy glue, buttons and motor screwdriver. The worm drive and the worm drive rack of the present invention are connected by the two part epoxy glue to the nylon strap, which is attached through rivet to the Boston Brace. The hexagonal peg makes it possible for the motor screwdriver to manipulate the worm drive, which determines the tightness of Boston brace. The button is attached to the worm drive rack, which makes it easy for the patients to unclasp the mechanism when taking off Boston Brace. With the help of above components, the scoliosis Boston brace can be assembled and the patients can use it to treat scoliosis.

DETAILED DESCRIPTION OF THE DRAWINGS

The present invention discloses an improved Scoliosis Boston Brace having a motorized tightening mechanism, which tightens the brace around the patient's body automatically with a motorized tightening mechanism, without any human intervention. The elimination of manual tightening by the present invention, paves way of firm and correct tightening of the brace, which helps in increased comfort for the patients.

With the help of the present invention, the patients can make use of automatic tightening technique which helps to tighten the Scoliosis Boston brace to the maximum degree.

The components of the present invention includes a Boston brace, a worm drive, worm drive rack, a hexagonal peg, nylon strap, rivet, two parts epoxy glue, buttons and motor screwdriver. The present invention can be understood in detail with the help of drawings.

Figure 1:
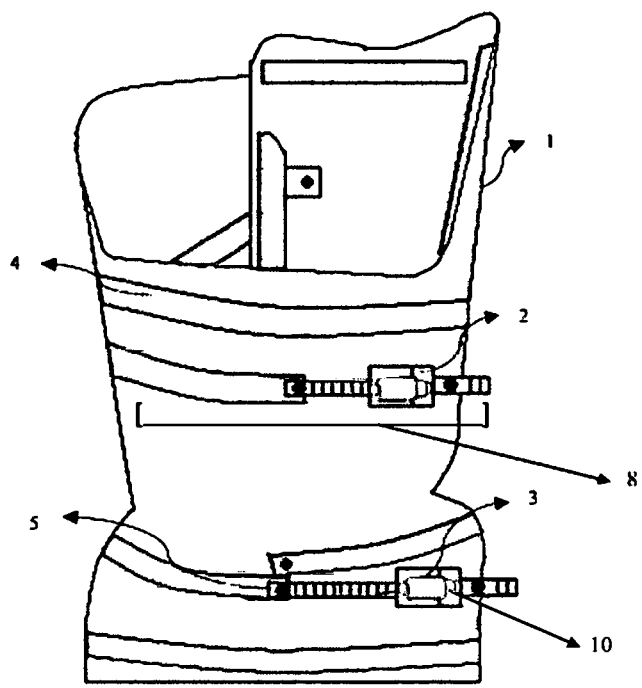
FIG. 1 is the front view of the scoliosis Boston brace with a motorized tightening mechanism, which can be used by the patients suffering from scoliosis.

Referring to FIG. 1, it is shown that the Boston brace with a motorized tightening mechanism constructed according to the present invention wherein the brace is represented by the reference number 1. The boston brace 1 is made up of outer layer of substantially rigid material.

The motorized tightening mechanism consists of the worm drive rack 3 and the worm drive 2, and nylon strap 4 which serves as the control for the tightness of the brace and determines how much pressure is applied. The worm drive 2 and the worm drive rack 3 of the present invention are connected together by the two part epoxy glue. The worm drive rack 3 is attached to the nylon fastener straps 4 through rivet 5. The nylon fastener straps are wrapped around the brace body 1.

Figure 2:
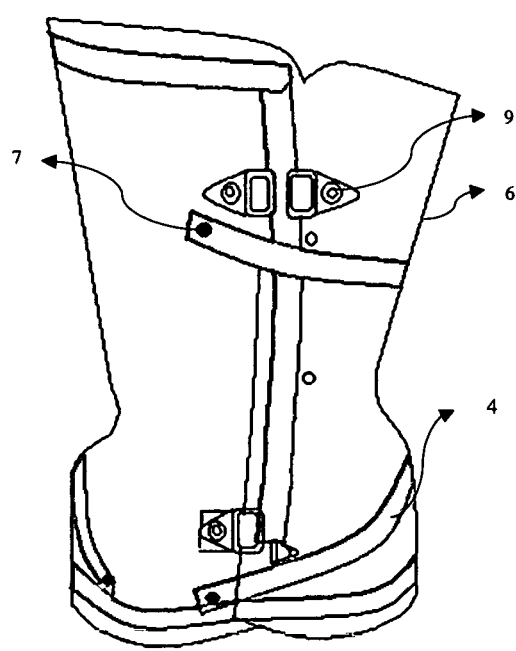
FIG. 2 is the back view of the Boston brace with the motorized tightening mechanism.

Referring to FIG. 2, the back side 6 of the Boston brace is shown. The brace is sealed by wrapping of the nylon fastener straps 4 around the brace body 1 and are fixed on the brace with the help of rivets/screws 7.

Figure 3:
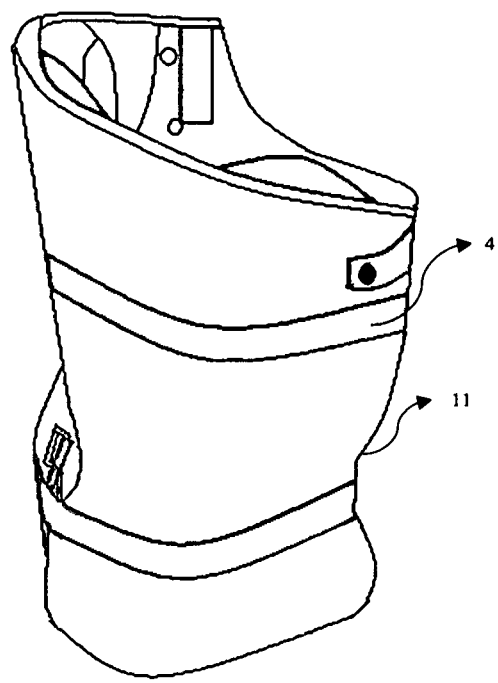
FIG. 3 is the side view of the Boston brace with the motorized tightening mechanism.

Referring to FIG. 3, it shows the side view 11 of the boston brace 1. The side view shows the inside curving of the brace at the bottom of the boston brace 1. This curve serves the purpose of accurate fitting along the torso of the patient such that the curve fixes around the waist of the patient.

Figure 4:
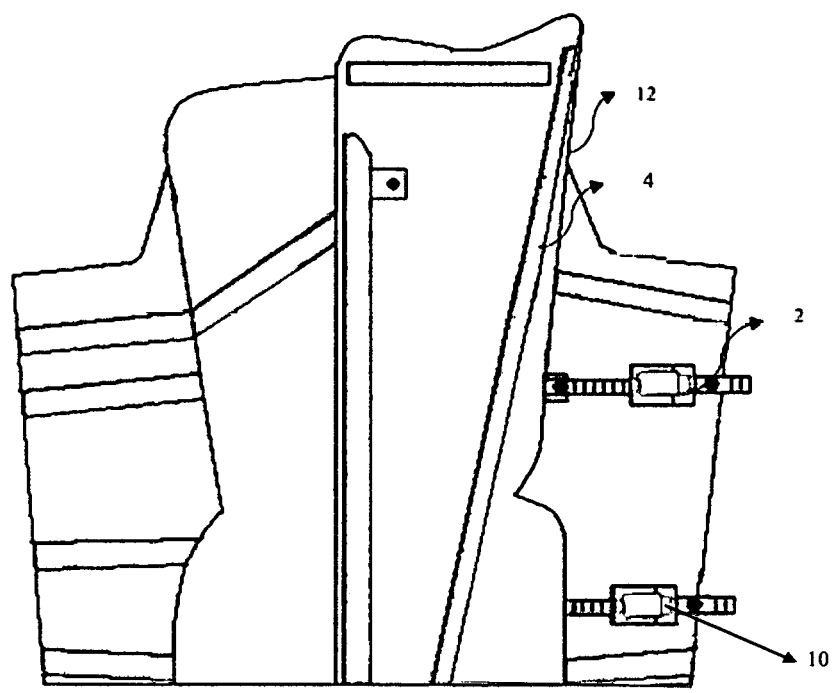
FIG. 4 is the front view of the scoliosis brace with the motorized tightening mechanism, where the scoliosis brace is in open position.

FIG. 4 is the front view of the scoliosis brace, where the scoliosis brace is in open position. The scoliosis brace 12 when in open position, discloses the nylon straps 4 which are in open position. The motorized tightening mechanism 8, is comprised of the nylon straps 4, the worm drive 2, and rack 3, which are measured and cut according to required length. The worm drive rack 3 is attached to the nylon strap 4 at two position using two part epoxy glue and the rivet. The scoliosis brace 12 also has buttons which are glued to the scoliosis brace 12 using two part epoxy glue, where the other side of the button is attached to the worm rack 3, which is also in open position.

The hexagonal peg 10 makes it possible for a motor screwdriver to manipulate the worm drive 5, which determines the tightness of boston brace. A motorized screwdriver is used to turn the hexagonal peg 10, which is the main driving force that actually moves the worm drive 2, thus tightening the brace 1.

With the help of above components, the scoliosis Boston brace can be assembled and the patients can use it to treat scoliosis.

In order to set-up the scoliosis boston brace, all the above mentioned components of the present invention has to be gathered together. The nylon strap 4 and the worm drive rack 3 has to be cut according to the required length; the worm drive rack 3 has to be attached to the nylon strap 4 using two part epoxy glue and the rivet 5; the nylon strap 4 has to be attached to the boston brace 1 using rivet 7. The same steps are repeated to connect the bottom strap as well in order to assemble the scoliosis boston brace. The worm rack 3 has to be cut to the preferred measurement, which directly correlates with the range of pressure that moving the worm drive 2 along the rack will be able to provide. Similarly the nylon strap 4 has to be cut the preferred measurement so that it fits to wrap around the brace, all the way past the opening in the back. Finally the hexagonal peg 10 has to be attached to an external motor so that the user can easily move the worm drive 2. This completes the assembly of the scoliosis boston brace of the present invention.

The technology used in the present invention provides a more efficient solution for the scoliosis problems. In order to operate the scoliosis boston brace, the user would have to attach the hexagonal peg which is connected to the motor, to the worm drive, and then turn on the motor to navigate the worm drive along the worm rack. This mechanism tightens the brace automatically. When the user would have to remove the brace, the motor has to be turned in the opposite direction, which loosens the worm drive, until the worm drive and worm rack are disconnected from each other.

The scoliosis boston brace is a basically type of thoracolumbo-sacral-orthosis (TLSO), which is a back brace primarily for the treatment of idiopathic scoliosis. The Scoliosis Boston brace comprises of an outer covering preferably made of high density polypropylene, polyethylene foam, or plastic. The Scoliosis Boston brace is corrects the curves in the lumbar or thoraco-lumbar part of the spine. It is primarily designed in such a way as to keep the lumbar area of the body in a flexed position by pushing the abdomen in and flattening the posterior lumbar contour. The brace exerts pressure at certain areas of the body in order to provide relief from the pain.

According to the present invention, the manual tightening the brace is inconvenient and imprecise. The scoliosis boston brace described in the present invention is automatic, easy to put on or wear and tighten. The brace is highly accurate as it relies on technology rather than manual tightening. The motorized tightening mechanism of the scoliosis brace ensures that the brace is tightened firmly, which leads to a higher chance of brace success and helps to avoid spine surgery.

We claim:

1. An improved scoliosis brace comprising:
   a. a boston brace;
   b. a worm drive element having worm drive and worm drive rack;
   c. a hexagonal peg;
   d. nylon strap, rivet, two parts epoxy glue and buttons; and
   e. a motor screwdriver;
   wherein, the worm drive element consists of the worm drive rack and the worm drive which serves as a control for the tightness of the brace and determines an amount of pressure applied; the worm drive elements are connected together by the two part epoxy glue; the nylon fasteners are attached to the worm drive element to wrap around a brace body which is attached through rivet to the boston brace.

2. An improved scoliosis brace as cited in claim 1 wherein, the scoliosis brace has a motorized tightening mechanism, which tightens the brace that is adapted to the patient's body automatically with a motorized tightening mechanism, without any human intervention.

3. An improved scoliosis brace as cited in claim 1 wherein, the scoliosis brace has front side and back side, which is made up of outer layer of rigid material.

4. An improved scoliosis brace as cited in claim 1 wherein, a scoliosis brace is adapted to the patient's torso with two edges that slightly overlap and seal the brace at the back side of the patient along the spine, with the help of nylon fastener straps.

5. An improved scoliosis brace cited in claim 1 wherein, the scoliosis boston brace includes a length management of the nylon strap and the worm drive rack of the required length, and the worm drive rack is attached to the nylon strap using two part epoxy glue and the rivet; the nylon strap is attached to the boston brace using rivet, which is carried out to connect both the top and bottom straps to the scoliosis brace.

6. An improved scoliosis brace cited in claim 1 wherein, the worm rack of the preferred measurement, which provides necessary tightness to the patient.

7. An improved scoliosis brace cited in claim 1 wherein, the hexagonal peg is attached to a motor for easy movement of the worm drive.

8. An method of operation of the scoliosis brace of claim 1 comprising:
   a. placing the scoliosis brace on the torso of the patient;
   b. attachment of the hexagonal peg connected to the motor and to the worm drive;
   c. turn on the motor to navigate the worm drive along the worm rack;
   d. tightening of the brace automatically with the movement of the worm rack, where the brace exerts pressure at certain areas of the body in order to provide relief from the pain;
   e. turning off the motor in an opposite direction to loosen the worm drive until the worm drive and worm rack are disconnected from each other; and
   f. removal of a scoliosis boston brace from the body of the patient.

* * * * *